United States Patent [19]

Van Roekel

[11] Patent Number: 5,641,496

[45] Date of Patent: Jun. 24, 1997

[54] TRANSPORT PACKAGE FOR SPECIMEN CONTAINERS

[76] Inventor: John H. Van Roekel, 306 Eden Hills Rd., Siler City, N.C. 27344

[21] Appl. No.: 579,797

[22] Filed: Dec. 28, 1995

Related U.S. Application Data

[62] Division of Ser. No. 229,722, Apr. 19, 1994, Pat. No. 5,503,835.

[51] Int. Cl.$^6$ .................................................. A01N 25/08
[52] U.S. Cl. .......................... 424/404; 424/411; 424/412; 424/413
[58] Field of Search ........................... 206/534, 811, 206/524.4, 459.1; 436/1, 3, 147, 169; 424/404, 405, 412–416; 604/360–362

[56] References Cited

U.S. PATENT DOCUMENTS

| | | |
|---|---|---|
| 1,516,454 | 11/1924 | Norton . |
| 3,041,184 | 6/1962 | Hartshorne .................. 99/174 |
| 3,899,295 | 8/1975 | Halpern ........................ 23/253 |
| 4,098,577 | 7/1978 | Halpern ........................ 23/232 |
| 4,853,266 | 8/1989 | Cullen ........................ 421/35.7 |
| 4,865,855 | 9/1989 | Hansen et al. .............. 426/124 |
| 4,888,175 | 12/1989 | Burton, Jr. et al. ......... 424/409 |
| 4,908,215 | 3/1990 | Perlman ...................... 424/661 |
| 5,372,429 | 12/1994 | Beaver, Jr. et al. .......... 383/109 |

OTHER PUBLICATIONS

Sattar and Springthorpe, Survival and Disinfectant Inactivation of the Human Immunodeficiency Virus: A Critical Review, Rev. of Infectious Diseases 1991; 13:430–437.

*Primary Examiner*—Neil S. Levy
*Attorney, Agent, or Firm*—Olive & Olive, P.A.

[57] ABSTRACT

A package for a container of a sample such as a medical specimen, which includes a sealable absorbent envelope for holding the container as the main structural component of the package. The package also includes an impermeable layer which surrounds the sealed envelope. Preferably the package also comprises one or both of: at least one antibiotic substance, associated with the envelope, which is capable of inhibiting at least one target microorganism which may be present in the sample; and an indicator for leakage associated with the envelope.

7 Claims, 1 Drawing Sheet

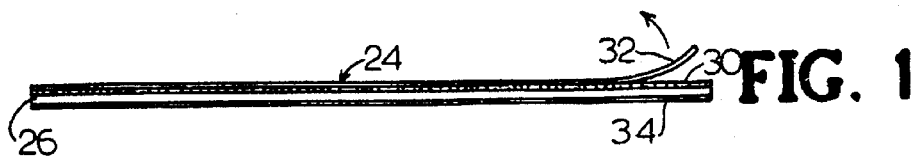
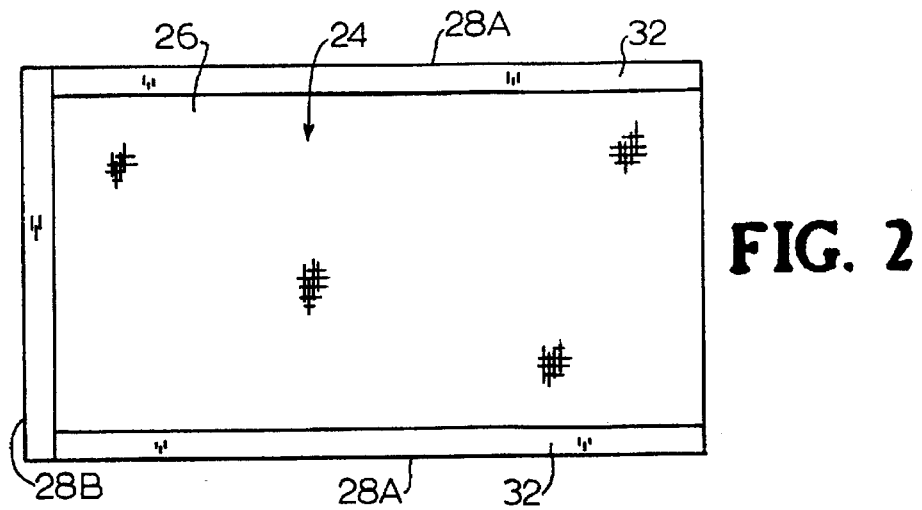
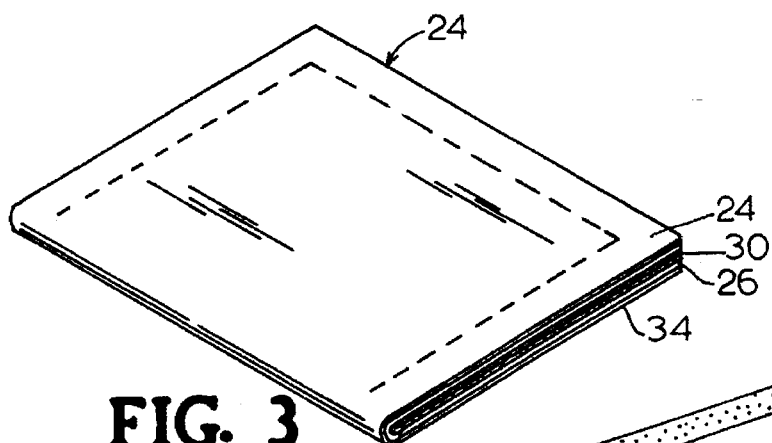
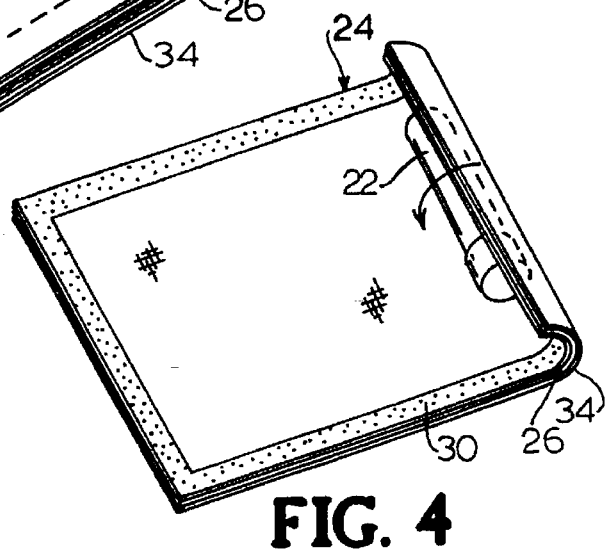
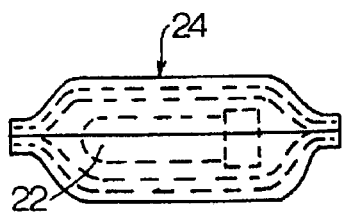

TRANSPORT PACKAGE FOR SPECIMEN CONTAINERS

CROSS-REFERENCE TO RELATED APPLICATIONS

This application is a divisional of application Ser. No. 08/229,722, filed Apr. 19, 1994, now U.S. Pat. No. 5,503,835.

BACKGROUND OF THE INVENTION

1. Field of the Invention

This invention relates to new and useful improvements in packaging, and in particular, pertains to packaging for medical specimens.

2. Description of the Related Art

Patient specimens which are to be analyzed in a medical laboratory often must be transported or shipped from the collection site to the laboratory which may be in another building or in another more remote geographic area. Such shipments increase the risk of breakage or leaking of the specimen containers during transport. Persons handling the specimens during or after shipment thus may be exposed to hazardous infective agents which may be present in the specimens such as viruses, for example, the HIV virus responsible for AIDS or the hepatitis virus, infectious bacteria, fungi, and protozoans.

It is therefore an object of this invention to provide a package and method for inhibiting the activity and infectiousness of any pathogens or other infective agents which may be released during breakage or leaking of specimen containers, and for reducing the likelihood of accidental contamination by a specimen which has been or is being transported from one site to another.

It is a further object of this invention to provide a package and a method for indicating when leaking of a specimen container has occurred in the package.

Other objects and advantages will be more fully apparent from the following disclosure and appended claims.

SUMMARY OF THE INVENTION

The invention herein is a package for a container of a sample such as a medical specimen. The main structural component of the package is a sealable absorbent envelope for holding said container. The invention also includes an impermeable layer which surrounds the sealed envelope. Preferably the package also comprises one or both of: at least one antibiotic substance, associated with the envelope, which is capable of inhibiting at least one target microorganism which may be present in the sample; and an indicator for leakage associated with the envelope.

Other aspects and features of the invention will be more fully apparent from the following disclosure and appended claims.

BRIEF DESCRIPTION OF THE DRAWINGS

FIG. 1 is a cross-sectional view of an envelope of the invention.

FIG. 2 is a planar view of the side of the envelope of FIG. 1 which contains cover strips over adhesive areas.

FIG. 3 is a perspective view of an envelope folded for insertion of a specimen container according to one preferred embodiment of the invention.

FIG. 4 is a perspective view of an envelope of the invention beginning to be rolled around a specimen container according to a second preferred embodiment of the invention.

FIG. 5 is a perspective view of the envelope of FIG. 4 completely rolled around a specimen container.

DETAILED DESCRIPTION OF THE INVENTION AND PREFERRED EMBODIMENTS THEREOF

The present invention is a package for a container 22 of a sample, which in its preferred embodiment comprises:

(a) a sealable absorbent envelope 24 for holding said container 22;

(b) an antibiotic substance, associated with said envelope, which is capable of inhibiting at least one microorganism which may be present in said sample; and (c) an indicator for leakage associated with said envelope 24.

The invention also includes the process of preparing the envelope. The absorbent envelope 24 may be made of a rectangular sheet 26 of material formed as shown in FIGS. 1-3. Selected edges 28A, B of the sheet 26 of absorbent paper or other material used to make the envelope 24 preferably are coated or impregnated with a strip of adhesive material 30. Preferably two opposite parallel edges 28A of the rectangular sheet and at least one other edge 28B are coated with the adhesive material 30. The adhesive material 30 is covered with a removable cover, made for example, of a strip 32 of waxed paper as is now used for covering the flaps of mailing envelopes until the envelopes are sealed.

Preferably, to use the envelope 24 with a sample container 22, the envelope 24 is partially assembled by selectively removing some of the strips 32 before or after inserting a sample container 22. The remaining strips 32 are removed to make the final seal to hold the inserted sample container 22. As shown in FIG. 3, after removal of the strips 32 on the two parallel sides 28A, the sheet may be folded in half. The sample container 22 may then be inserted, and the remaining strip 28B removed to seal the container 22 into the envelope 24.

Alternatively, the strips 32 on the two parallel sides 28A may be removed and the sheet 26 may be rolled around the sample container 22 parallel to the two parallel sides 28A (FIGS. 4-5). After the sheet 26 is almost completely rolled around the sample container 22, the remaining strip 32 can be removed to expose the final adhesive portion 30 and all of the adhesive-coated surfaces can be pressed toward the adjacent portions of sheet material to seal all of the edges.

It is also within the scope of the invention as contemplated herein to devise other means of configuring the sheet of material to seal it around sample containers, particularly for irregularly shaped sample containers. In some cases, additional or larger adhesive areas may be provided to allow for greater flexibility in sealing position or more secure sealing.

The absorbent envelope 24 may be made of any absorbent substance which is formable into a bendable sheet and to which an adhesive may be attached. Preferred substances for making the absorbent envelope include filter paper, for example, Whatman No. 40 filter paper stock, cotton and/or rayon, or other absorbent material.

Adhesives which may be used are preferably self-adhesive so that when the protective strip is removed the adhesively-coated areas will stick to each other. Such adhesives are well known in the art, and can be of any one of many different types. Thus, such pressure-sensitive, self-sealing adhesives as are used for labels and envelopes (e.g., U.S. Pat. No. 5,201,982) may be used. The disclosure of this patent and all other patents cited herein is incorporated herein by reference. Usable self-adhesive adhesives include, for example, tacky polymers, (e.g., U.S. Pat. No. 5,234,736), silicone compositions (U.S. Pat. No. 4,254,644) and acrylate co-polymers (U.S. Pat. No. 5,258,479). In addition, the adhesive preferably provides a liquid-tight closure of the edge of the envelope (e.g., as is provided by U.S. Pat. No. 5,205,649).

The absorbent envelope 24 of the invention is most preferably made of a sheet of absorbent material which is bonded or otherwise attached to a layer of impermeable material 34 as is shown in FIG. 1. Such materials are known for use, for example, in diapers. The impermeable material 34 is preferably one or more layers or sheets of a water-impermeable plastic material such as polyethylene or other plastic materials known in the art. If no such layer is associated directly with the absorbent envelope, it is preferred that, before transport or handling, the assembled envelope be placed in another outer impermeable package, such as a sealable plastic bag (not shown).

All or a majority of the absorbent envelope is preferably treated with an antibiotic substance (not shown). As used herein, the term "antibiotic substance" means one or more chemical substances which inactivate, or inhibit activity and/or multiplication of one or more selected microorganisms which might be present in a particular sample or specimen to an acceptable level as is known in the art. Microorganisms for the purpose of this definition include any hazardous or potentially hazardous bacteria, fungi, viruses or genetic entity which might be present in the sample or specimen.

Preferred antibiotic substances are broadly antimicrobial such as chlorine-based disinfectants (e.g., sodium hypochlorite), phenolics (e.g., LYSOL™), and antimicrobial detergents (e.g., Nonidet p-40™), so that all likely pathogens will be inactivated or killed. Alternatively, for particular specimens having a likely limited range of pathogens, more tailored antibiotic substances may be used if desired.

The antibiotic substances to be used also are preferably stable disinfectants upon drying and rewetting, so that the envelope can be treated with the antibiotic substance and dried prior to use for transport of specimen container. The preferred antibiotic substances also have a relatively short contact time required for inhibition or killing of at least the target microorganisms to be inhibited or killed for particular types of specimens. Preferably the antibiotic substance(s) used are not themselves particularly noxious or toxic to humans.

Preferably the antibiotic substance(s) have a pH different from that of the specimens, and/or are buffered at a different pH, so that only when there is specimen leakage, will the indicator(s) change color, as the pH of the wetted envelope changes due to the leakage.

The above characteristics are well-documented for many disinfectants and other antimicrobial substances, and persons of skill in the art can easily choose those most suitable for the particular selected purpose. A list including such potentially useful antibiotic substances is found, for example, in Sattar and Springthorpe, *Survival and Disinfectant Inactivation of the Human Immunodeficiency Virus: A Critical Review, Reviews of Infectious Diseases* 13: 430–447 (1991). A few of the antibiotic substances listed are: sodium hypochlorite, chlorine dioxide, glutaraldehyde, formaldehyde, formaldehyde+Beta-propiolactone, Beta-propiolactone, alcohols, hydrogen peroxide, and iodophors.

The concentration of antibiotic substance to be used is dependent on the chosen antibiotic substance, the target microorganism(s), particularly if particularly difficult to inactivate or kill, and the likely volume of liquid which might leak from the sample container. Thus, the antibiotic substance present in or on the absorbent envelope should be acceptably inhibitory if a small volume of the specimen wets a portion of the envelope or if the entire contents of the specimen container is released into the absorbent envelope. Preferably this concentration of antibiotic substance would provide such inhibition in a relatively short time, for example, within 5–10 minutes of the leakage.

For example, it is known (see review of Sattar and Springthorpe, referenced above) that a 0.5% solution of sodium hypochlorite for 5 minutes will provide a greater than 7-log inactivation of an initial inoculum size of $10^{10.5}$ (50% tissue culture infectious dose) of HIV viruses in 50% human plasma. A 10-minute exposure to a dilution to give 0.08% of a mixture of quaternary ammonium compounds containing 1.536% octyldecyldimethyl $NH_4CL$, 0.768% dioctyldimethyl $NH_4CL$, 0.768% N-docyldimethyl $NH_4CL$ and 12.288% alkyldimethylbenzyl $NH_4CL$ provides a greater than 7-log inactivation of an initial inoculum size of $10^{10.5}$ (50% tissue culture infectious dose) of HIV viruses in 50% human plasma. A 0.5% solution of the detergent Nonidet p-40 for 1–15 minutes provides a greater than 8-log inactivation of an initial inoculum size of $10^{1.5}$ (50% tissue culture infectious dose) of HIV viruses in 50% human plasma. Similar information is available in the literature and is known to one of skill in the art regarding various antibiotic substances which might be used in the invention and various potential pathogens which might be present in the specimen.

The treatment of the absorbent envelope is preferably by saturation of the absorbent material with the antibiotic substance followed by drying. Thus, when a specimen container enclosed in the envelope later leaks, the liquid from the container dissolves or suspends the antibiotic substance in or on the envelope as the liquid comes in contact with the envelope. The antibiotic substance is thus present in the liquid that might contain the hazardous or harmful microorganisms from the container, so that inhibition and/or killing of the microorganisms may occur.

For use with specimens suspected of containing harmful viruses or virus particles, or bacteria, the absorbent envelope is treated with at least one antiviral substance or at least one antibacterial substance, respectively. Because most specimens have the possibility of containing both viruses and bacteria, preferably the antibiotic substance(s) used contain at least one antiviral and one antibacterial compound, or a compound or mixture of compounds which together are antibacterial and antiviral.

The preferred embodiment of the transport package of the invention also includes a leakage indicator substance or a plurality of such substances. Most preferably the indicator is a pH indicator which will show a color change when the absorbent envelope and any associated antimicrobial substance(s) are wetted by a specimen leaking from a container. It is known that blood has a pH of about 7.35–7.45 and urine has a pH in the range of about 4.8–7.5. This information is available in a standard chemical or physiological chemistry text (see, for example, Chang, *Chemistry*, 1991, McGraw-Hill, Inc., page 642).

Therefore, a pH indicator for blood serum leakage would need to indicate a change of pH to a neutral pH (about pH 7.4) and an indicator for urine leakage from a specimen container would need to show a pH change in the indicator (or indicators) if the indicator was exposed to liquid in the pH range from about 4.8 to 7.5. The latter indicator(s) would also show a change if they were wetted by leaking blood serum, and are therefore preferred so that the same package can be used for either type of physiological specimen. For other specimens having different likely pH values, other indicators which will show a color change at that pH as are known in the art should be used.

Examples of indicators for use with either blood serum or urine samples include such well-known pH indicators as xylenol blue, M-cresol purple, bromcresol green, o-cresol red, cyanidine chloride, bromcresol purple, alizarin, thymol blue, brom cresol red, methyl red, acid fuchsin, brilliant yellow, logwood extract, bromthymol blue, phenol red, phenolphthalein, and the like, as well as the alkali and alkaline earth salts, and other pH indicators. Other indicators specific for blood serum, urine or other specific fluids, or components thereof, as are known in the art, may be employed. In addition, any indicator(s) which change color upon being wetted, and retain that color even if redried would also be utilizable as part of the invention. Each of these indicators may be applied to the envelope at any of the standard concentrations as they are used in media as are known in the art, so that when the envelope is wetted with the contents of the specimen, the final concentration of the indicator is such that a color change will be observed. For example, phenol red used at a concentration in the range of about 0.018 g/liter based on the average volume of the specimen which might wet the envelope.

Although the preferred embodiment comprises both an antibiotic and a leakage indicator, it is contemplated that in particular instances only one of these components might be included. For example, for transport of a multitude of containers in large sealed containers, the primary goal might be to kill any microorganisms which might leak out of the container, without inspection for leakage or further use of the individual sample containers.

The preferred utilization of the invention is for one specimen container per envelope, but the invention, particularly when constructed of a larger size sheet of absorbent material may be used to contain multiple containers, so long as the grouping of the containers does not compromise safety or patient identity concerns. Such grouping would thus be contemplated to be primarily useful for transport of a small number of containers to a disposal site after analysis.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A package for a container which contains a liquid which is suspected of containing hazardous microorganisms of a specimen, comprising:
   (a) a sealable absorbent envelope for holding said container, said envelope being treated with:
      i. an antibiotic substance, in an amount which is sufficient to inhibit at least one of said hazardous microorganisms; and
      ii. a pH indicator for detecting leakage of said liquid from said container, wherein a visible change in the indicator substance on the absorbent envelope indicates leakage of the liquid from the container.

2. A package according to claim 1, wherein said envelope is made of absorbent filter paper.

3. A package according to claim 1, wherein said envelope comprises adhesive strips on a plurality of edges of said envelope for sealing said envelope.

4. A package according to claim 1, wherein said antibiotic substance is selected from the group consisting of chlorine-based disinfectants, phenolics and antimicrobial detergents.

5. A package according to claim 4, wherein said antibiotic substance is sodium hypochlorite.

6. A package according to claim 1, wherein said indicator is selected from the group consisting of xylenol blue, M-cresol purple, bromcresol green, o-cresol red, cyanidine chloride, bromcresol purple, alizarin, thymol blue, brom cresol red, methyl red, acid fuchsin, brilliant yellow, logwood extract, bromthymol blue, phenol red, and phenolphthalein.

7. A package according to claim 6, wherein said indicator is phenol red.

* * * * *